United States Patent
Giampapa et al.

(10) Patent No.: US 9,345,733 B1
(45) Date of Patent: May 24, 2016

(54) SUPPLEMENT COMPOSITION FOR SUPPORTING TELOMERE MAINTENANCE AND PROTECTION AND METHOD OF USE

(75) Inventors: Vincent C. Giampapa, Montclair, NJ (US); David B. Cross, Chappaqua, NY (US)

(73) Assignee: CELLHEALTH TECHNOLOGIES LTD., Montclair, NJ (US)

( * ) Notice: Subject to any disclaimer, the term of this patent is extended or adjusted under 35 U.S.C. 154(b) by 127 days.

(21) Appl. No.: 13/573,406

(22) Filed: Sep. 13, 2012

Related U.S. Application Data

(60) Provisional application No. 61/534,708, filed on Sep. 14, 2011.

(51) Int. Cl.

| | |
|---|---|
| A61K 36/16 | (2006.01) |
| A61K 36/28 | (2006.01) |
| A61K 31/05 | (2006.01) |
| A61K 31/197 | (2006.01) |
| A61K 31/198 | (2006.01) |
| A61K 31/7048 | (2006.01) |
| A61K 36/258 | (2006.01) |

(52) U.S. Cl.
CPC .......... *A61K 36/28* (2013.01); *A61K 31/05* (2013.01); *A61K 31/197* (2013.01); *A61K 31/198* (2013.01); *A61K 31/7048* (2013.01); *A61K 36/16* (2013.01); *A61K 36/258* (2013.01)

(58) Field of Classification Search
None
See application file for complete search history.

(56) References Cited

U.S. PATENT DOCUMENTS

| | | | | |
|---|---|---|---|---|
| 6,646,013 | B1 * | 11/2003 | Barker et al. ............... | 514/731 |
| 2009/0169623 | A1 * | 7/2009 | Sene et al. ............... | 424/474 |

OTHER PUBLICATIONS

2013. Retrieved from: <URL: http://www.enzolifesciences.com/browse/nitric-oxide-pathway/>.*
Leong et al., Signaling pathways mediated by tumor necrosis factor alpha, 2000, Histol Histopathol, 15: 1303-25.*
Selhub, Homocysteine metabolism, 1999, Annu Rev Nutr, 19: 217-46.*
Lin et al., Renaturation and Stabilization of the Telomere-Binding Activity of *Saccharomyces* Cdc13(451-693)p by L-Arginine, 2001, Analytical Biochemistry, 294: 44-47.*
Ahn, Jiyun, et al., "Resveratrol inhibits TNF-α-induced changes of adipokines in 3T3-L1 adipocytes." Biochemical and Biophysical Research Communications, 2007, vol. 364, pp. 972-977, Elsevier Inc.
Bannwart, C. F., et al., "Inhibitory effect of silibinin on tumour necrosis factor-alpha and hydrogen peroxide production by human monocytes." Natural Product Research, Nov. 2010, vol. 24, No. 18, pp. 1747-1757, Taylor & Francis.
Bereswill, Stefan, et al., "Anti-Inflammatory Effects of Resveratrol, Curcumin and Simvastatin in Acute Small Intestinal Inflammation," PLoS One, Dec. 2010, vol. 5, Issue 12, e15099, pp. 1-11, © Bereswill et al.
Bourraindeloup, Marie, et al., "N-Acetylcysteine Treatment Normalizes Serum Tumor Necrosis Factor-α Level and Hinders the Progression of Cardiac Injury in Hypertensive Rats," Circulation, Oct. 5, 2004, vol. 110, pp. 2003-2009, American Heart Association, Inc.
Cailleret, Michel, et al., "N-Acetylcysteine Prevents the Deleterious Effect of Tumor Necrosis Factor-α on Calcium Transients and Contraction in Adult Rat Cardiomyocytes," Circulation, Jan. 27, 2004, vol. 109, pp. 406-411, The American Heart Association, Inc.
Chandler, Dave, et al., "Effects of plant-derived polyphenols on TNF-α and nitric oxide production induced by advanced glycation endproducts," Mol. Nutr. Food Res., 2010, vol. 54, pp. S141-S150, Wiley-VCH Verlag GmbH & Co. KGaA, Weinheim.
Chou, Tz-Chong, et al., "The Antiinflammatory and Analgesic Effects of Baicalin in Carrageenan-Evoked Thermal Hyperalgesia," Anesth Analg, 2003, vol. 97, pp. 1724-1729, International Anesthesia Research Society.
Coronel, Israel, et al., "L-Arginine and Antioxidant Diet Supplementation Partially Restores Nitric Oxide-Dependent Regulation of Phenylephrine Renal Vasoconstriction in Diabetics Rats," Journal of Renal Nutrition, May 1, 2010, vol. 20, Issue 3, 14 pages, National Kidney Foundation, Inc.
Cui, A., "N-acetylcysteine inhibits TNF-α, sTNFR, and TGF-β 1 release by alveolar macrophages in idiopathic pulmonary fibrosis in vitro," *Sarcoidosis vasculitis* and Diffuse Lung Diseases, 2009, vol. 26, pp. 147-154, Mattioli 1885.
Dong, Xie Xu, et al., "Ginkgo Biloba Extract Reduces Endothelial Progenitor-Cell Senescence Through Augmentation of Telomerase Activity," J Cardiovasc Pharmacol™, Feb. 2007, vol. 49, No. 2, pp. 111-115, Lippincott Williams & Wilkins.
Effros, Rita B., "Telomere/telomerase dynamics within the human immune system: effect of chronic infection and stress," Author Manuscript, 2010, pp. 1-12, Elsevier Inc. [Exp Gerontol., 2011, pp. 135-140, vol. 46, No. 2-3].
Förstermann, Ulrich, et al., "Therapeutic effect of enhancing endothelial nitric oxide synthase (eNOS) expression and preventing eNOS uncoupling," British Journal of Pharmacology, 2011, vol. 164, pp. 213-223, The British Pharmacological Society.
Fossel, Michael, et al., "Telomerase and Human Disease: The Beginnings of the Ends?" Rejuvenation Research, Nov. 5, 2009, vol. 12, No. 5, pp. 333-340, Mary Ann Liebert, Inc.

(Continued)

*Primary Examiner* — Terry A McKelvey
*Assistant Examiner* — Catheryne Chen
(74) *Attorney, Agent, or Firm* — Melvin K. Silverman

(57) ABSTRACT

A supplement composition for supporting telomere maintenance and protection, including effective amounts of extract of *silybum marianum*; N-acetylcysteine; Resveratrol; Extract of *Panax ginseng*; Extract of *Ginkgo biloba*; Puerarin; and L-arginine.

Further disclosed is a method for supporting telomere maintenance and protection, comprising orally administering a supplement composition to a person one or twice daily, said supplement composition comprising in one dosage: from about 100 mg to about 300 mg of extract of *silybum marianum*, from about 400 mg to about 600 mg of N-acetylcysteine, from about 40 mg to about 60 mg of trans-resveratrol, from about 80 mg to about 120 mg of extract of *Panax ginseng*, from about 40 mg to about 60 mg of extract of *ginkgo biloba*, and from about 80 mg to about 120 mg of puerarin, and from about 400 mg to about 600 mg of L-arginine.

4 Claims, No Drawings

(56) References Cited

OTHER PUBLICATIONS

Hayashi, Toshio, et al., "Endothelial cellular senescence is inhibited by nitric oxide: Implications in atherosclerosis associated with menopause and diabetes," PNAS, Nov. 7, 2006, vol. 103, No. 45, pp. 17018-17023, The National Academy of Sciences of the USA.

Liu, Xiao-Ju, et al., "The effects of genistein and puerarin on the activation of nuclear factor-κB and the production of tumor necrosis factor-α in asthma patients," Pharmazie, 2010, vol. 65, pp. 127-131.

Ma, Zeng-Chun, et al., "Ginsenoside Rg1 inhibits proliferation of vascular smooth muscle cells stimulated by tumor necrosis factor-α1," Acta Pharmacologica Sinica, Aug. 2006, vol. 27, No. 8, pp. 1000-1006, CPS and SIMM.

Nazemian, Fatemeh, et al., "Effect of Silymarin Administration on TNF-α Serum Concentration in Peritoneal Dialysis Patients," Phytotheraphy Research, 2010, vol. 24, pp. 1654-1657, John Wiley & Sons, Ltd.

Parish, Stanley T., et al., "Modulation of T Lymphocyte Replicative Senescence via TNF-α Inhibition: Role of Caspase-3I," The Journal of Immunology, 2009, vol. 182, pp. 4237-4243, The American Association of Immunologists.

Parzonko, Andrzej, et al., "Silymarin Inhibits Endothelial Progenitor Cells' Senescence and Protects Against the Antiproliferative Activity of Rapamycin: Preliminary Study," J Cariovasc Pharmocol™, Dec. 2010, vol. 56, No. 6, pp. 610-618, Lippincott Wiliams & Wilkins.

Sánchez-Fidalgo, Susana, et al., "Dietary supplementation of resveratrol attenuates chronic colonic inflammation in mice," European Journal of Pharmacology, 2010, vol. 633, pp. 78-84, Elsevier B.V.

Schmitt, Christoph A., et al., "Modulation of endothelial nitric oxide by plant-derived products," Nitric Oxide, 2009, vol. 21, pp. 77-91, Elsevier Inc.

Schmitt, Christoph A., et al., "Effect of resveratrol on endothelial cell function: Molecular mechanisms," BioFactors, Sep./Oct. 2010, vol. 36, No. 5, pp. 342-349 plus one page copyright information, International Union of Biochemistry and Molecular Biology, Inc.

Schroecksnadel, Katharina, et al., "Anti-inflammatory compound resveratrol suppresses homocysteine formation in stimulated human peripheral blood mononuclear cells in vitro," Clin Chem Lab Med, 2005, vol. 43, No. 10, pp. 1084-1088, Walter de Gruyter.

Voghel, Guillaume, et al., "Chronic treatment with N-acetyl-cystein delays cellular senescence in endothelial cells isolated from a subgroup of atherosclerotic patients," Author Manuscript, 2008, pp. 1-21, Elsevier Ireland Ltd. [Mech Ageing Dev., May 2008, vol. 129, No. 5, pp. 261-270].

Wadsworth, Teri L., et al., "Effects of Ginkgo biloba extract (EGb 761) and quercetin on lipopolysaccharide-induced signaling pathways involved in the release of tumor necrosis factor-α," Biochemical Pharmacology, 2001, vol. 62, pp. 963-974, Elsevier Science Inc.

Xia, L., et al., "Resveratrol reduces endothelial progenitor cells senescence through augmentation of telomerase activity by Akt-dependent mechanisms," British Journal of Pharmacology, 2008, vol. 155, pp. 387-394, Macmillan Publishers Limited.

Zhang, Hong-Sheng, et al., "Ginsenoside Rg1 Inhibits Tumor Necrosis Factor-α (TNF-α)-Induced Human Arterial Smooth Muscle Cells (HASMCs) Proliferation," Journal of Cellular Biochemistry, 2006, vol. 98, pp. 1471-1481, Wiley-Liss, Inc.

Zhu, J. H., et al., "Homocysteine accelerates senescence and reduces proliferation of endothelial progenitor cells," Journal of Molecular and Cellular Cardiology, 2006, vol. 40, pp. 648-652, Elsevier Ltd.

Zhu, Junhui, et al., "Puerarin reduces endothelial progenitor cells senescence through augmentation of telomerase activity," Vascular Pharmacology, 2008, vol. 49, pp. 106-110, Elsevier Inc.

Remington, Joseph P., et al., "Remington's Pharmaceutical Sciences," 1990, Eighteenth Edition, Mack Publishing Co.

Filing receipt and specification for patent application entitled "Dietary Supplement System for Multifunctional Anti-Aging Management and Method of Use," by Vincent C. Giampapa, filed Sep. 13, 2012 as U.S. Appl. No. 13/573,386.

Filing receipt and specification for provisional patent application entitled "Supplement Composition for Supporting Telomere Maintenance and Protection and Method of Use," by Vincent C. Giampapa, et al., filed Sep. 14, 2011 as U.S. Appl. No. 61/534,708.

* cited by examiner

SUPPLEMENT COMPOSITION FOR SUPPORTING TELOMERE MAINTENANCE AND PROTECTION AND METHOD OF USE

CROSS REFERENCE TO RELATED APPLICATION

This application claims the benefit under 35 USC 119(e) provisional patent application Ser. No. 61/534,708, filed Sep. 14, 2011, which is hereby incorporated by reference in its entirety.

FIELD OF THE INVENTION

The present invention relates to dietary supplement compositions for supporting telomere maintenance and protection, and the method of use.

BACKGROUND OF THE INVENTION

A telomere is a region of repetitive DNA sequences at the end of a chromosome, which protects the end of the chromosome from deterioration or from fusion with neighbouring chromosomes. During cell division, enzymes that duplicate DNA cannot continue their duplication all the way to the end of chromosomes. If cells divided without telomeres, they would lose the ends of their chromosomes, and the necessary information they contain.

The telomeres are disposable buffers blocking the ends of the chromosomes, are consumed during cell division, and are replenished by an enzyme, telomerase reverse transcriptase. Human somatic cells without telomerase gradually lose telomeric sequences as a result of incomplete replication. As human telomeres shorten to a critical length, cells reach the limit of their replicative capacity and progress into a state called cell-senescence, or cell stasis. At this point, the cells no longer divide and are essentially nonfunctional. Therefore, the longer period of time that the cells can maintain a longer telomere, the more they can divide, serve as functional cells, and maintain functional organs throughout the body.

It has been reported that shortened telomeres and consequent inability to maintain normal tissue function may underlie most age-related disease. Telomerase has been repeatedly proposed as a uniquely effective intervention in age-related disease (Fossel, M. *Telomerase and Human Disease*, Nov. 23, 2009). On the other hand, it has also been reported that inhibition of tumor necrosis factor-alpha (TNF-a) with a receptor inhibitor significantly increases proliferative potential as well as telomerase activity (Effros R B., *Exp Gerontol.* 2011 February-March); and the delayed loss of CD28-T lymphocytes induced by inhibition of TNF-a coincided with the increased telomerase activity (Parish S T, et al, *J Immunol.* 2009 Apr. 1).

In addition, it is also known that homocysteine accelerates senescence and reduces proliferation of endothelial progenitor cells, leading to cellular dysfunction (Zhu J H. et al, *J Mol Cell Cardiol.* 2006 May; 40(5):648-52).

Therefore, it is desirable to provide a dietary supplement composition that supports telomere maintenance and protection, to reduce age-related disorders.

SUMMARY OF THE INVENTION

A supplement composition for supporting telomere maintenance and protection, comprising effective amounts of extract of *silybum marianum*; N-acetylcysteine; Resveratrol; Extract of *Panax ginseng*; Extract of *Ginkgo biloba*; Puerarin; and L-arginine.

Further disclosed is a method for supporting telomere maintenance and protection, comprising orally administering a supplement composition to a person one or twice daily, said supplement composition comprising in one dosage: from about 100 mg to about 300 mg of extract of *silybum marianum*, from about 400 mg to about 600 mg of N-acetylcysteine, from about 40 mg to about 60 mg of trans-resveratrol, from about 80 mg to about 120 mg of extract of *Panax ginseng*, from about 40 mg to about 60 mg of extract of *ginkgo biloba*, and from about 80 mg to about 120 mg of puerarin, and from about 400 mg to about 600 mg of L-arginine.

DETAILED DESCRIPTION OF THE INVENTION

In one aspect, the present invention provides a supplement composition for supporting telomere maintenance and protection. In some embodiments, the supplement composition comprises compounds that have the effect of activating telomerase, which results in lengthening telomeres; compounds that increase the production or bioavailability of the telomerase activator nitric oxide; compounds that have effect of inhibiting TNF-a, which leads to an increased telomerase activity; and compounds that reduce homocysteine level and thus combat the reduction in telomerase activity caused by homocysteine.

In some embodiments, the supplement composition comprises silymarin, N-acetylcysteine, trans-resveratrol, extract of *panax ginseng*, extract of *ginkgo biloba*, puerarin, L-arginine and pharmaceutically acceptable medium or excipients. Many of these components possess multiple properties, such as increasing production nitric oxide as well as inhibiting TNF-a, as described hereinafter in detail, which are beneficial in telomere maintenance and protection.

Unless defined otherwise, all technical and scientific terms used herein have the same meaning as commonly understood by one having ordinary skills in the art to which the invention belongs.

Silymarin is an extract of *silybum marianum*, also called milk thistle, of a plant of the Asteraceae family. Silymarin is a flavonolignane complex comprising silibinin A and B/silybin/silymarin I, isosilibinin A and B, silicristin/silymarin II, silidianin. It has been reported in study of the effect of silymarin that silymarin increases telomerase activity threefold, reduces the number of senescent cells and increases endothelial progenitor cells proliferative activity (up to 64%) in comparison with cells cultured with rapamycin alone (Parzonko A. et al, *J Cardiovasc Pharmacol.* 2010 Aug. 31).

Furthermore, silymarin suppresses the induction of tumor necrosis factor (TNF-a) and it was hypothesized that silymarin could decrease the serum concentration of TNF-a in peritoneal dialysis patients, and thus treat anaemia. It has been found in a clinical study that serum TNF-a of some patients decreased and in the response group the haemoglobin concentration after 8 weeks of silymarin administration increased significantly, indicating potential utility of silymarin in the treatment of inflammation (Nazemian F. et al, *Phytother Res.* 2010 November). It is further reported that silibinin (the major component of silymarin) exerts antioxidant and anti-inflammatory properties on human monocytes through an inhibitory effect on hydrogen peroxide release and on TNF-a production, respectively (Bannwart C F. et al, *Nat Prod Res.* 2010 November; 24(18): 1747-57). Additionally, it has also been found that silymarin inhibites BSA-advanced glycation endproducts-induced nitric oxide production, and reduces TNF-a expression (Chandler D. et al, *Mol Nutr Food Res.* 2010 July; 54 Suppl. 2:S141-50).

In some embodiments of the present invention, the supplement composition comprises silymarin, or extract of *silybum marianum* (standardized to about 80% silymarin), in an amount from about 100 mg to about 300 mg in one dosage. In one embodiment, the supplement composition comprises about 200 mg of extract of *silybum marianum* (standardized to about 80% silymarin) in one dosage.

Herein, one dosage is also referred to as one serving. If the supplement composition is provided in the form of capsule, one dosage can be either one capsule, or two to three capsules. For example, 200 mg of extract of *silybum marianum* in one dosage can be provided in one capsule or in two capsules. The size and number of capsule or tablet may depend on the manufacturability, which may further depend on the properties of the components and the pharmaceutically acceptable excipients used therein.

N-acetylcysteine is a glutathione precursor, and it is quickly metabolized into glutathione once it enters the body. Glutathione is an intracellular protein that plays an important role in the body's antioxidant defense system. Glutathione is also involved in maintenance of RNA and DNA. It has been shown that chronic exposure to N-acetyl-cysteine can delay senescence of diseased endothelial cells via activation of the catalytic subunit of telomerase (hTERT) and transient telomere stabilization, unless oxidative stress-associated cell damage has become irreversible. (Voghel G, et al, *Mech Ageing Dev.* 2008 May).

Furthermore, N-acetylcysteine is also a compound that inhibits TNF-a. It has been found that N-acetylcysteine prevents the deleterious effect of TNF-a on calcium transients and contraction in adult rat cardiomyocytes (Cailleret M. et al, *Circulation,* 2004 Jan. 27; 109(3):406-11). N-acetylcysteine treatment normalizes serum TNF-a level and hinders the progression of cardiac injury in hypertensive rats (Bourrain-deloup M. et al, *Circulation.* 2004 Oct. 5; 110(14):2003-9); and N-acetylcysteine inhibits TNF-a, sTNFR, and TGF-beta1 release by alveolar macrophages in idiopathic pulmonary fibrosis in vitro (Cu A, et al, *Sarcoidosis Vase Diffuse Lung Pis.,* 2009 July; 26(2):147-54).

In some embodiments of the present invention, the supplement composition comprises N-acetylcysteine in an amount from about 400 mg to about 600 mg in one dosage. In one embodiment, the supplement composition comprises about 500 mg of N-acetylcysteine in one dosage.

Resveratrol is a unique compound produced by the skins of grapes, grapevines and other plants and their roots in response to environmental stresses. It exists as two geometric isomers: cis-(Z) and trans-(E), and the trans-form can undergo isomerisation to the cis-form when exposed to ultraviolet irradiation. Trans-resveratrol in the powder form was found to be stable under the conditions of 75% humidity and 40° C. in the presence of air. Resveratrol content also is stable in the skins of grapes and pomace taken after fermentation and stored for a long period.

Resveratrol has been reported having potent antioxidant activity and having the ability to inhibit platelet aggregation. It is believed that resveratrol plays an important role in the repair and maintenance of DNA strands. Resveratrol is considered a candidate drug for prevention and treatment of cardiovascular diseases, and is a compound that increases the production or bioavailability of the telomerase activator nitric oxide. A number of in vivo and in vitro studies have shown that improved vascular function in response to resveratrol appeared to be at least partly due to increased nitric oxide availability (Schmitt C A et al, *Nitric Oxide* 2009 September). Molecular mechanisms on how resveratrol enhances endothelial nitric oxide production, improves endothelial redox balance and inhibits endothelial activation in response to pro-inflammatory and metabolic insults have been described (Schmitt C A, et al, *Biofactors.* 2010 September). Trans-resveratrol has been identified as one of the small molecules that have the potential to prevent endothelial nitric oxide synthase uncoupling and, at the same time, enhance endothelial nitric oxide synthase expression. Such compounds also enhance nitric oxide production from endothelial nitric oxide synthase under pathophysiological conditions and may thus have therapeutic potential (Forstermann U. et al, *Br J Pharmacol.* 2010 Dec. 30). Moreover, it has further been found that resveratrol delayed the onset of endothelial progenitor cells senescence and this effect was accompanied by activation of telomerase through the PI3K-Akt signalling pathway. (Xia L, et al, *Br J Pharmacol.* 2008 October).

On the other hand, resveratrol is a compound that inhibits TNF-a, which leads to increase of telomerase activity. It has been found that resveratrol inhibits TNF-a induced changes of adipokines (Ahn J. et al, *Biochem Biophys Res Commun.* 2007 Dec. 28; 364(4):972-7); and that pro-inflammatory cytokine expression (IL-23p19, IFN-y, TNF-a, IL-6, MCP-1) is found to be significantly lower in the ileum of animals treated with resveratrol (Bereswill S. et al, *PLoS One.* 2010 Dec. 3). Dietary supplementation of resveratrol attenuates chronic colonic inflammation in mice by causing substantial reductions of the rise of pro-inflammatory cytokines, TNF-a and IL-1β and an increase of the anti-inflammatory cytokine IL-10 (Sanchez-Fidalqo S. et al, *Eur J Pharmacol.* 2010 May 10).

In addition, resveratrol is also a compound that reduces homocysteine levels, and thus combats the reduction in telomerase activity caused by homocysteine. It has been found that resveratrol suppresses homocysteine formation in stimulated human peripheral blood mononuclear cells in vitro, (Schroecksnadel K. et al, *Clin Chem Lab Med.* 2005; 43(10): 1084-8).

In some embodiments of the present invention, trans-resveratrol from *polygonum cuspidatum* or from grape skin extract is used. In some embodiments, the supplement composition comprises trans-resveratrol in an amount from about 40 mg to about 60 mg in one dosage. In one example, the supplement composition comprises about 50 mg of trans-resveratrol in one dosage.

*Panax ginseng* roots are traditionally taken orally as adaptogens, aphrodisiacs, nourishing stimulants, and in the treatment of type II diabetes, as well as for sexual dysfunction in men. Ginsenosides are the active compounds that distinguish the *Panax* species. It has been found that *panax ginseng* root aqueous extract rapidly activates endothelial nitric oxide synthase via the PI3K/Akt-pathway in human umbilical vein endothelial cells (HUVEC). This effect might be mediated by the triterpen saponin ginsenoside Rg1, which induces endothelial nitric oxide synthase phosphorylation via Akt at nanomolar concentrations in HUVEC. Similarly, ginsenoside Rb1 acutely induces endothelial nitric oxide synthase-Ser1177 phosphorylation and nitric oxide production in human aortic endothelial cells (Schmitt C A. et al, *Nitric Oxide,* 2009 September).

Furthermore, extract of *panax ginseng* has the effect of inhibiting TNF-a. It has been found that ginsenoside Rg1 inhibits proliferation of vascular smooth muscle cells stimulated by tumor necrosis factor-alpha (Ma Z C, et al, *Acta Pharmacol Sin.* 2006 August; 27(8):1000-6); and that ginsenoside Rg1 inhibits TNF-a-induced human arterial smooth muscle cells (HASMCs) proliferation (Zhang H S, et al. *J Cell Biochem.* 2006 Aug. 15; 98(6): 1471-81).

In the present invention, the supplement composition comprises extract of *panax ginseng* for increasing the production or bioavailability of the telomerase activator nitric oxide and inhibiting TNF-a to increase telomere activity. In some embodiment, the supplement composition comprises extract of *panax ginseng* that has high levels of ginsenosides Rg1/Rh1. The extract of *panax ginseng* can be in an amount from about 80 mg to about 120 mg in one dosage. In one embodiment, the supplement composition comprises about 100 mg of extract of *panax ginseng* in one dosage.

Extracts of *ginkgo biloba* leaves contain flavonoid glycosides and terpenoids (ginkgolides, bilobalides) and have been used pharmaceutically. It has been found that extract of *ginkgo biloba* leaves increased endothelial nitric oxide synthase expression, endothelial nitric oxide synthase-Sern77 phosphorylation and improved coronary artery circulation in patients with coronary artery disease (Schmitt C A. et al, *Nitric Oxide,* 2009 September). Furthermore, in-vitro studies have shown that *ginkgo biloba* extract increases endothelial progenitor-cell numbers and functional activity, and that *ginkgo biloba* extract delays the onset of endothelial progenitor-cell senescence, which may be related to activation of telomerase through the PI3k/Akt signaling pathway. This indicates that the inhibition of endothelial progenitor-cell senescence by *ginkgo biloba* extract in vitro may improve the functional activity of endothelial progenitor-cells in a way that is important for potential cell therapy. (Dong, X. et al, *J Cardiovasc Pharmacol.* 2007 February).

Furthermore, the extract of *ginkgo biloba* has the effect of inhibiting TNF-a. It has been found that pretreatment with *Ginkgo biloba* extract (EGb 761) inhibited the in vivo production of TNF-a after challenge with bacterial lipopolysaccharide (Wadsworth T L, *Biochem Pharmacol.* 2001 Oct. 1; 62(7):963-74).

In some embodiments of the present invention, the supplement composition comprises extract of *ginkgo biloba*, in an amount from about 40 mg to about 60 mg in one dosage. In one embodiment, the supplement composition comprises about 50 mg of extract of *ginkgo biloba* in one dosage.

Puerarin is one of several known isoflavones. Puerarin is found in a number of plants and herbs like the root of radix puerariae. In-vitro study has shown that puerarin dose dependently prevents the onset of endothelial progenitor cells senescence in culture and increases proliferation of endothelial progenitor cells. The effect of puerarin in delaying the onset of endothelial progenitor cells senescence may be related to the activation of telomerase through the PI-3K/Akt pathway (Zhu J. et al, *Vascul Pharmacol.* 2008 August-September; 49(2-3): 106-10).

Furthermore, puerarin has the effect of inhibiting TNF-a. In-vitro study of the effect of puerarin on activation of NF-κB and production of TNF-a in peripheral blood mononuclear cells of asthma patients has shown that puerarin could inhibit the pathway of NF-κB and TNF-a in asthma patients (Liu X J et al, *Pharmazie.* 2010 February; 65(2):127-31).

In some embodiments of the present invention, the supplement composition comprises puerarin derived from radix puerariae in an amount from about 80 mg to about 120 mg in one dosage. In one embodiment, the supplement composition comprises about 100 mg of puerarin in one dosage.

L-arginine is one of the 20 most common natural amino acids and it is a precursor of nitric oxide. Arginine plays an important role in cell division, healing of wounds, removing ammonia from the body, immune function and the release of hormones. It has been found that the ingestion of nitric oxide boosting substances, including L-arginine, L-citrulline, and antioxidants, can delay endothelial senescence under high glucose; and when L-arginine, L-citrulline and antioxidants were given together, the recovery of nitrite production was more marked (Louis J. et al., *Proc Natl Acad Sci USA.* 2006 November). Animal studies further show that restoration of the protective nitric oxide mechanism may be achieved by simultaneously stimulating nitric oxide synthesis and preventing the effects of reactive oxygen species through the use of L-arginine and a combination of vitamins E and C as diet supplementation. (Coronel I, et al., *J Ren Nutr.* 2010 May).

In some embodiments of the present invention, the supplement composition comprises L-arginine, in an amount from about 400 mg to about 600 mg in one dosage. In one embodiment, the supplement composition comprises about 500 mg of L-arginine in one dosage.

Baicalin, a flavonoid isolated from *Scutellaria baicalensis* Georgi, is a traditional Chinese herbal medicine used for cardiovascular dysfunction. It has been suggested that the anti-inflammatory and analgesic mechanisms of baicalin may be associated with the inhibition of critical inflammatory mediators, including nitric oxide, PGE2, and proinflammatory cytokines, accompanied by an increase in IL-10 production, as well as neutrophil infiltration at sites of inflammation (Tz-Chong Chou, et al, *Anesth Analg* 2003; 97:1724-9)

Optionally, in some embodiments of the present invention, the supplement composition may further comprise Baicalin from *Scutellaria baicalensis* Georgi in an amount from about 50 mg to about 150 mg in one dosage. In one example, the supplement composition comprises about 100 mg of Baicalin in one dosage.

All above described active components used in the illustrative, or preferred embodiments such as silymarin, N-acetylcysteine, trans-resveratrol, extract of *panax ginseng*, extract of *ginkgo biloba*, puerarin, L-arginine, baicalin are commercially available. Example 1 illustrates an exemplary supplement composition of the present invention.

The effects of the supplement composition of the present invention in supporting telomere maintenance and protection can be understood in several aspects. The supplement composition of the present invention supports reducing oxidative stress and inflammation, and enhancing DNA repair, and therefore, it supports maintaining existing telomere length by reducing the rate of telomere shortening. Moreover, the supplement composition facilitates maintenance of existing levels of endogenous telomerase activity. Furthermore, the supplement composition stimulates telomerase activity via exogenous telomerase activators to the extent that helps maintain telomerase production. Increasing telomerase activity ultimately results in increase and/or maintenance of telomere length.

As convenient forms of dietary supplement, the supplement compositions described above can be provided in the form of tablet or capsule. When other dosage forms are used, the amounts of the active components in one dosage or serving remain the same.

The supplement compositions can be formulated as tablet, capsule or liquid, containing pharmaceutically acceptable medium or excipients, according to methods and procedures well known in the art. As used herein, "excipients" means substances that are of little or no therapeutic value, but useful in the manufacture and compounding of various pharmaceutical preparations, which form the medium of the supplement compositions. The substances may include coloring, flavoring, and diluting agents, emulsifying and suspending agents, ointment bases, pharmaceutical solvents, antioxidants and preservatives for the product, and miscellaneous agents. Suitable excipients are described in Remington's Pharmaceutical Sciences, Mack Publishing Company, a standard reference text in this field, which is incorporated herein by reference in its entirety.

As used herein, "diluting agents" are inert substances added to increase the bulk of the formulation to make a tablet a practical size for compression. Commonly used diluting agents include calcium phosphate, calcium sulfate, lactose, kaolin, mannitol, sodium chloride, dry starch, powdered sugar, silica, and other suitable materials. As used herein, "binders" are agents used to impart cohesive qualities to the powdered material. Binders insure the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and other suitable materials. In one embodiment, the pharmaceutically acceptable medium includes dicalcium phosphate, microcrystalline cellulose, croscarmellose sodium, stearic acid, magnesium stearate, silica, and pharmaceutical glaze.

In another aspect, the present invention provides the method of using the supplement compositions described above as a dietary supplement to individuals, particularly those in need thereof. Preferably, the supplement composition is orally administrated one or more times daily, more preferably twice a day. In one embodiment, the supplemental composition is orally administrated twice a day, once in the morning and once in the evening; and each serving, or one dosage, includes from about 100 mg to about 300 mg of extract of *silybum marianum*, from about 400 mg to about 600 mg of N-acetylcysteine, from about 40 mg to about 60 mg of trans-resveratrol, from about 80 mg to about 120 mg of extract of *panax ginseng*, from about 40 mg to about 60 mg of extract of *ginkgo biloba*, and from about 80 mg to about 120 mg of puerarin, and from about 400 mg to about 600 mg of L-arginine.

Furthermore, the supplement compositions of the present invention can also be used in conjunction with other dietary supplements, such as multiple vitamins and other suitable supplements. In one example, the supplement compositions of the present invention can be used together with a supplement system described in a co-pending patent application entitled "Dietary Supplement System for Multifunctional Anti-Aging Management and Method of Use". This supplement system includes two compositions for oral administration in the morning and evening, respectively. The use of the present composition in addition to said supplement system further enhances the effect in telomere maintenance and protection, particularly suitable for those in need thereof.

The following examples are illustrative of the invention and are in no way to be interpreted as limiting the scope of the invention, as defined in the claims.

EXAMPLE 1

A composition of the following formulation was prepared in the form of tablet, including pharmaceutically acceptable excipients, by methods known to those of ordinary skill in the art:

TABLE 1

Supplement Composition

| Contents | Amount Per Serving |
|---|---|
| Extract of *silybum marianum* (standardized to 80% silymarin) | 200 mg |
| N-acetylcysteine | 500 mg |
| Trans-resveratrol from *Polygonum cuspidatum* | 50 mg |
| Extract of *Panax ginseng* | 100 mg |
| Extract of *gingko biloba* | 50 mg |
| Puerarin derived from *Radix puerariae* | 100 mg |
| L-arginine | 500 mg |

Other ingredients include: dicalcium phosphate, microcrystalline cellulose, croscarmellose sodium, stearic acid, magnesium stearate, silica, and pharmaceutical glaze.

Each patent, patent application, publication, text and literature article or report cited or indicated herein is hereby expressly incorporated by reference in its entirety.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

What is claimed is:

1. A method for increasing telomerase activity comprising orally administering a supplement composition to a person one or twice daily, said supplement composition comprising in one dosage: 200 mg of extract of *silybum marianum* standardized to 80% silymarin, 500 mg of N-acetylcysteine, 50 mg of trans-resveratrol from *Polygonum cuspidatum,* 100 mg of extract of *Panax ginseng,* 50 mg of extract of *ginkgo biloba,* 100 mg of puerarin derived from Radix puerariae, and 500 mg of L-arginine, magnesium sterate, silica, and pharmaceutical glaze.

2. The method of claim 1 comprising administering the composition in an morning dose and evening dose.

3. The method of claim 1 comprising administering a second supplement composition wherein the second supplement composition comprises a multivitamin.

4. The method of claim 3 comprising administering the second supplement composition in a morning and evening dose.

* * * * *